United States Patent [19]

Byrd

[11] Patent Number: 5,529,062
[45] Date of Patent: Jun. 25, 1996

[54] TRACHEOSTOMY TUBE HOLDER AND ASSOCIATED TUBE HOLDING METHOD

[76] Inventor: Timothy N. Byrd, 1267 Old Cades Cove Rd., Townsend, Tenn. 37882

[21] Appl. No.: 433,234

[22] Filed: May 2, 1995

[51] Int. Cl.⁶ .......................... A61M 25/02; A61M 16/00
[52] U.S. Cl. ............................ 128/207.17; 128/DIG. 26; 128/200.26; 128/207.14; 604/179; 604/180
[58] Field of Search ................. 128/200.26, 207.14, 128/207.16, 207.17, 911, 912, DIG. 23, DIG. 26; 606/155, 156; 604/171, 174, 177, 178, 179, 188

[56] References Cited

U.S. PATENT DOCUMENTS

| | | | |
|---|---|---|---|
| D. 310,721 | 9/1990 | Beisang, III | D24/49 |
| 3,046,989 | 7/1962 | Hill | 128/348 |
| 3,826,254 | 7/1974 | Mellor | 128/133 |
| 3,927,676 | 10/1975 | Schultz | 128/351 |
| 3,977,407 | 8/1976 | Coleman et al. | 128/348 |
| 4,120,304 | 10/1978 | Moor | 128/348 |
| 4,142,527 | 3/1979 | Garcia | 239/348 |
| 4,249,529 | 2/1981 | Nestor et al. | 128/207.17 |
| 4,331,144 | 5/1982 | Wapner | 128/207.17 |
| 4,333,468 | 6/1982 | Geist | 128/348 |
| 4,351,331 | 9/1982 | Gereg | 128/207.17 |
| 4,489,723 | 12/1984 | Simons et al. | 128/207.16 |
| 4,548,200 | 10/1985 | Wapner | 128/207.17 |
| 4,583,976 | 4/1986 | Ferguson | 604/174 |
| 4,690,675 | 9/1987 | Katz | 604/177 |
| 4,744,358 | 5/1988 | McGinnis | 128/207.17 |
| 4,774,944 | 10/1988 | Mischinski | 128/207.17 |
| 4,823,789 | 4/1989 | Besang, III | 128/207.18 |
| 4,836,200 | 6/1989 | Clark | 128/207.18 |
| 4,932,943 | 6/1990 | Nowak | 604/180 |
| 5,037,397 | 8/1991 | Kalt et al. | 604/174 |
| 5,215,532 | 6/1993 | Atkinson | 604/180 |

*Primary Examiner*—Edgar S. Burr
*Assistant Examiner*—Virendra Srivastava
*Attorney, Agent, or Firm*—Pitts & Brittian

[57] ABSTRACT

A tracheostomy tube holder for being received about a patient for maintaining the position of a tracheostomy tube and an associated tube holding method. The tracheostomy tube holder (10) includes first and second tube engaging assemblies (14, 16) for engaging the tracheostomy tube (11). Each of the tube engaging assemblies (14, 16) has a first foundation strap (24) defining an outer bonding surface (30) proximate its distal end portion, and carries a tube engaging strap (36) for engaging the tracheostomy tube (11), with the tube engaging strap (36) having a distal end portion for being positioned on the first bonding surface (30). Each of the tube engaging assemblies (14, 16) further includes a locking strap (36) having a proximal end secured to the foundation strap (24) and defining an inner adhesive surface (44) for releasably engaging both the distal end portion of the tube engaging strap (36) and the outer bonding surface (30) of the foundation strap (24).

9 Claims, 7 Drawing Sheets

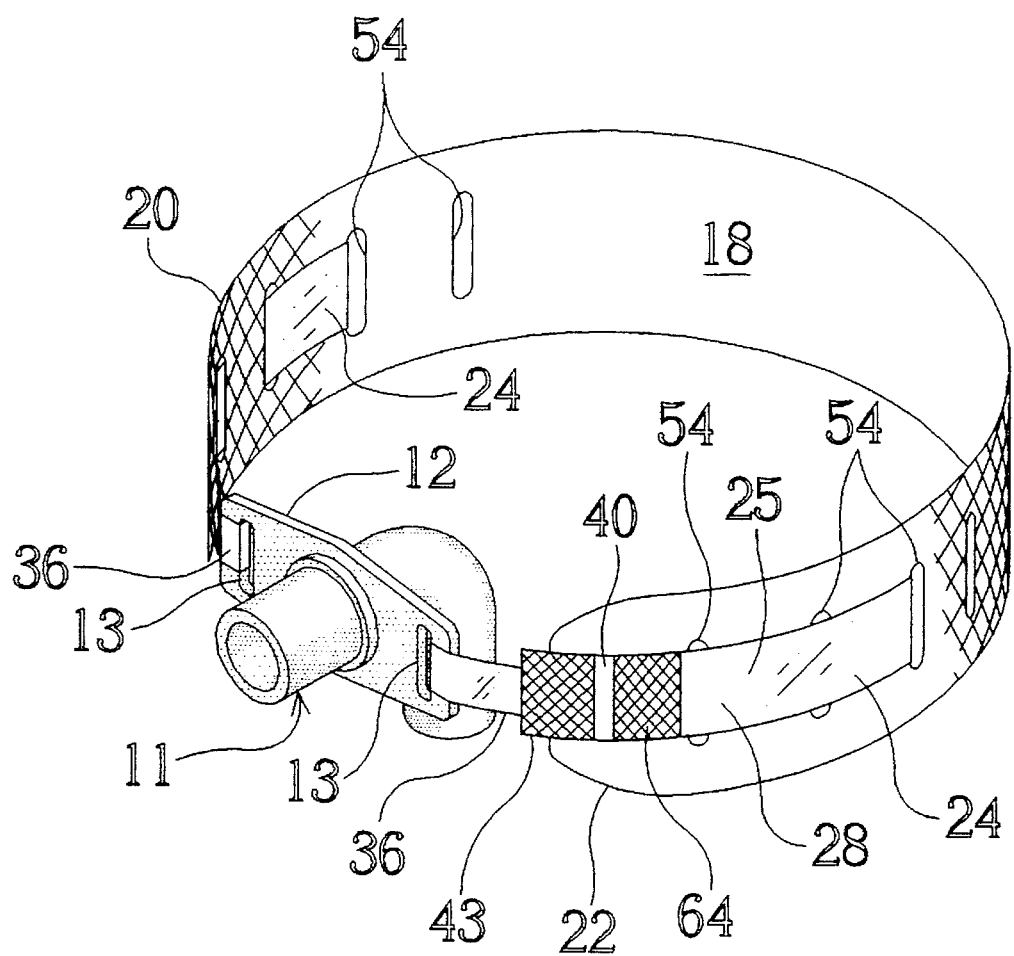

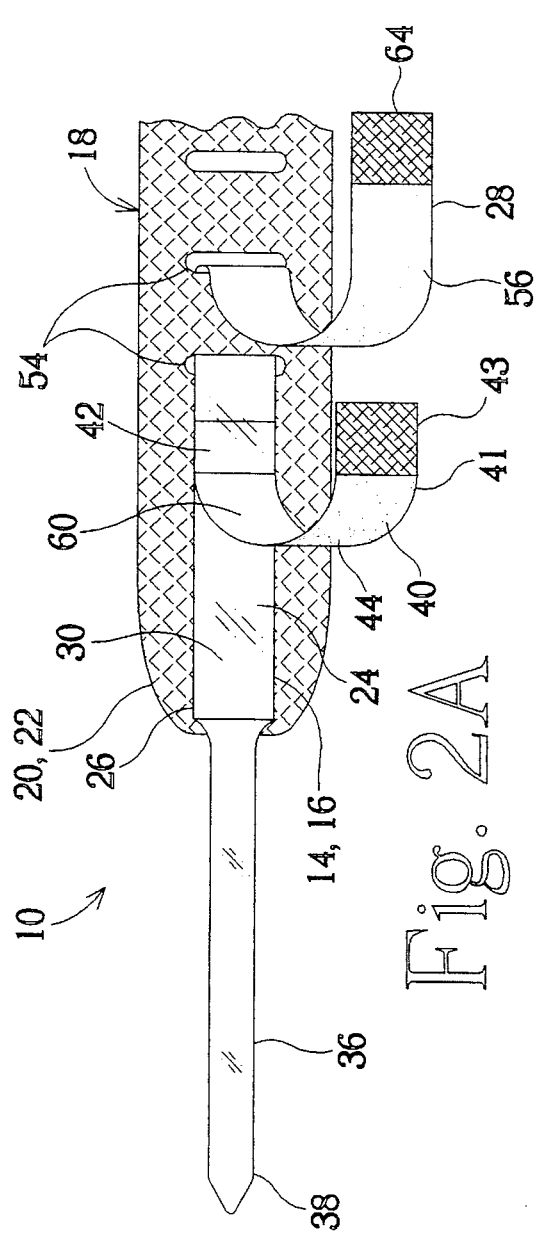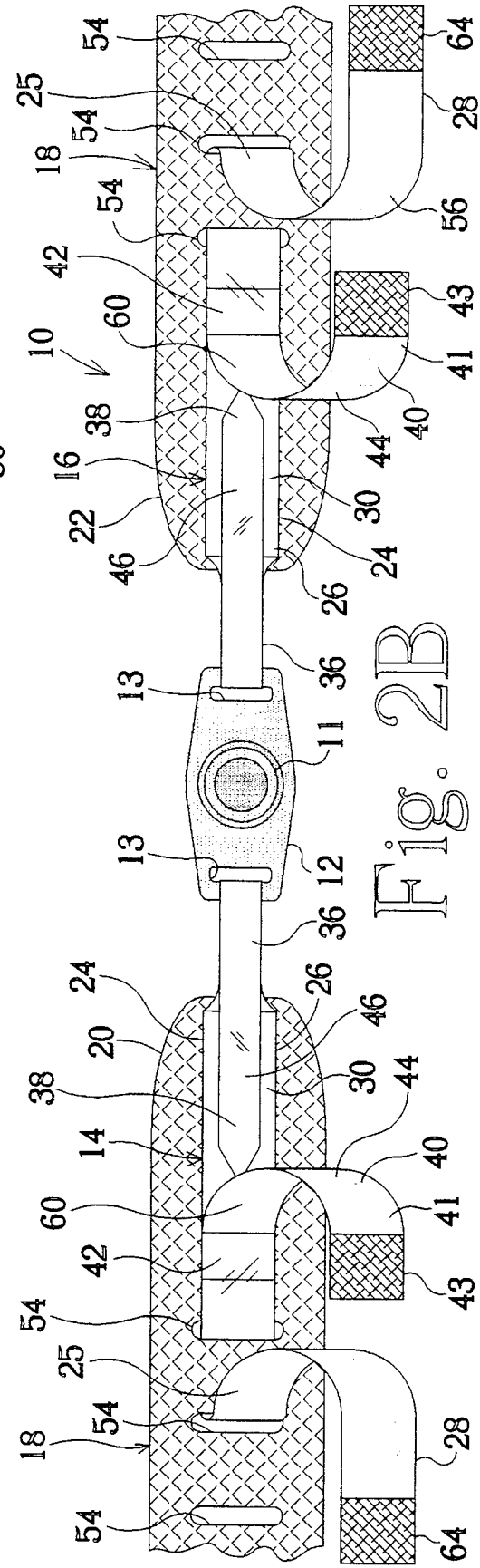

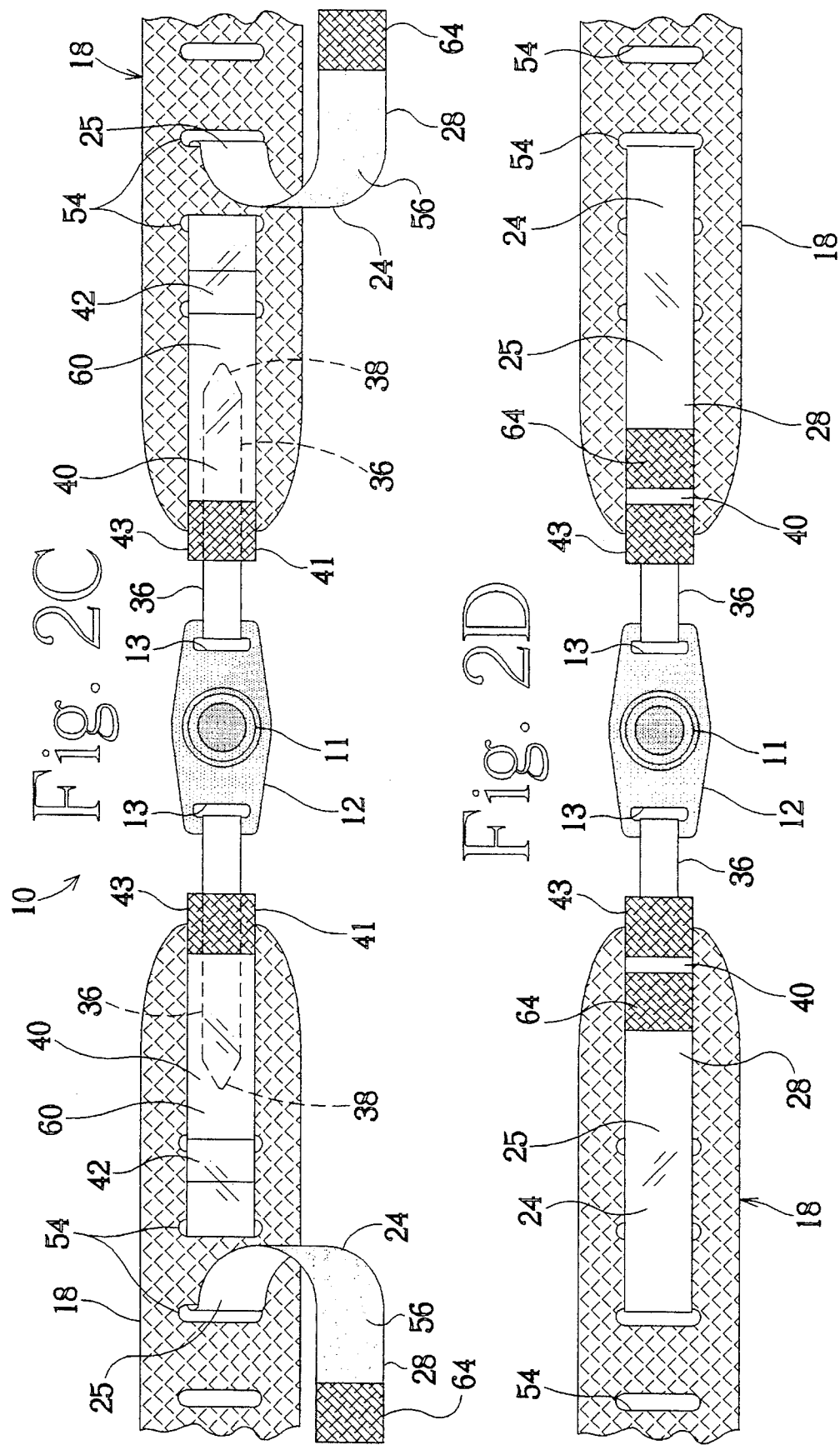

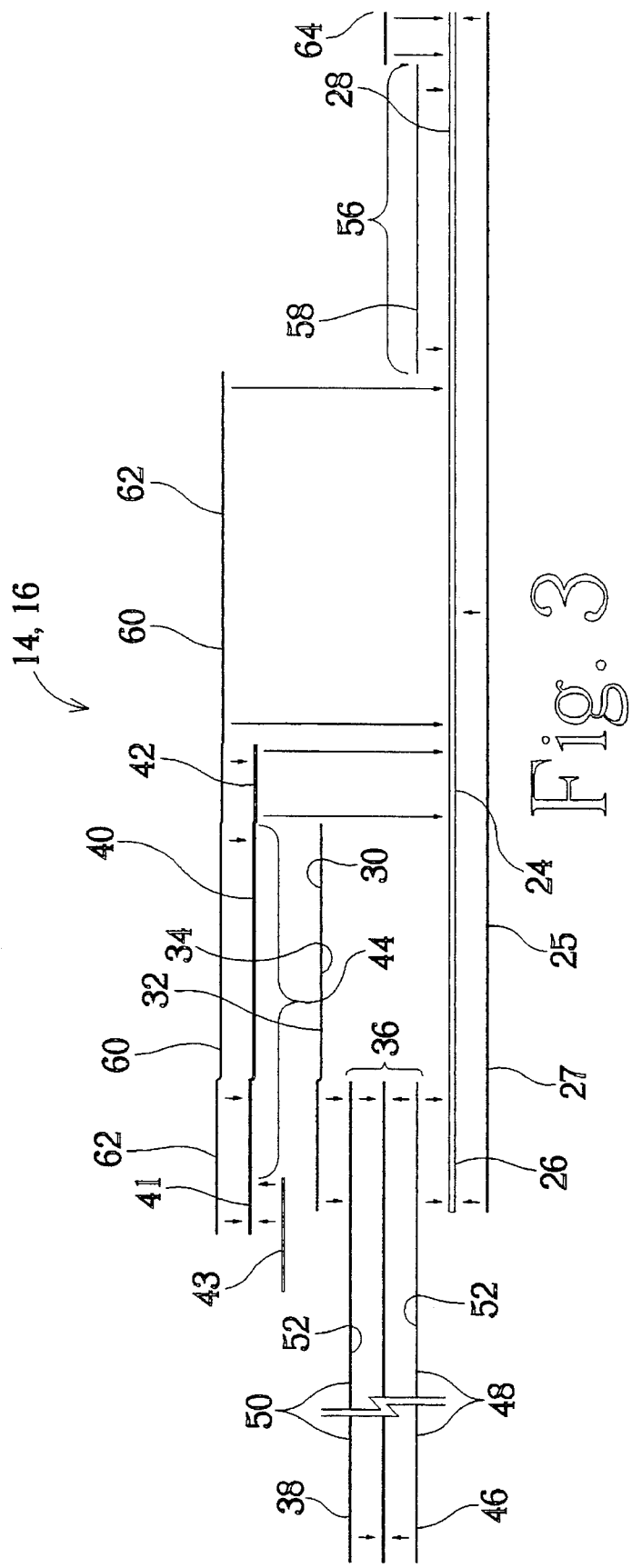

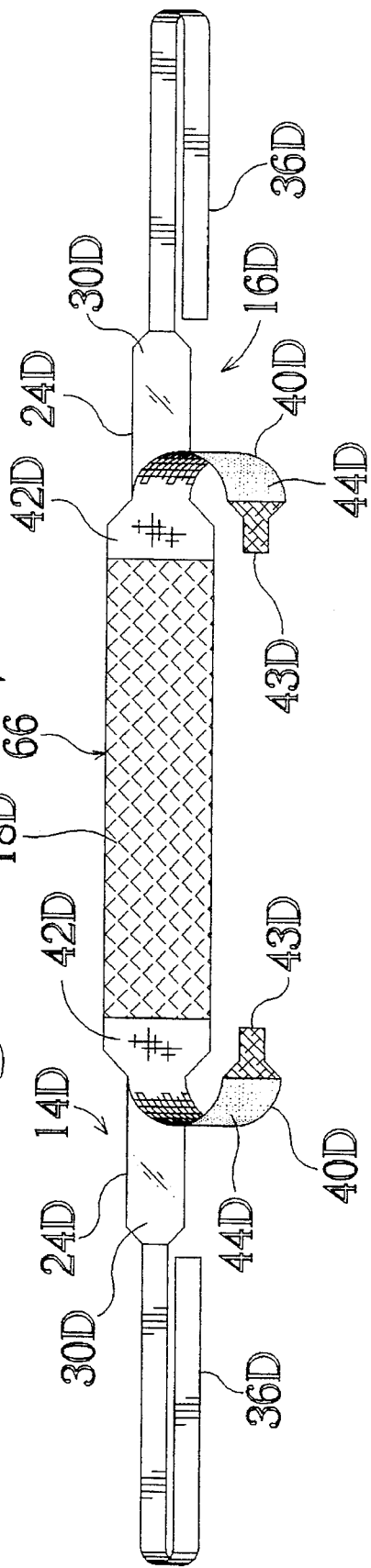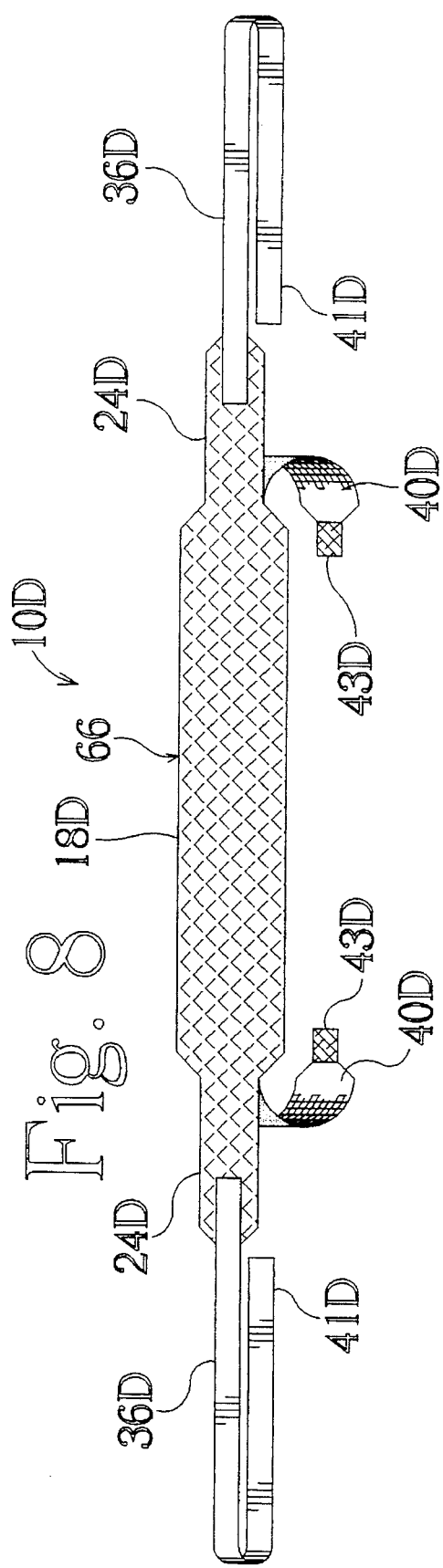

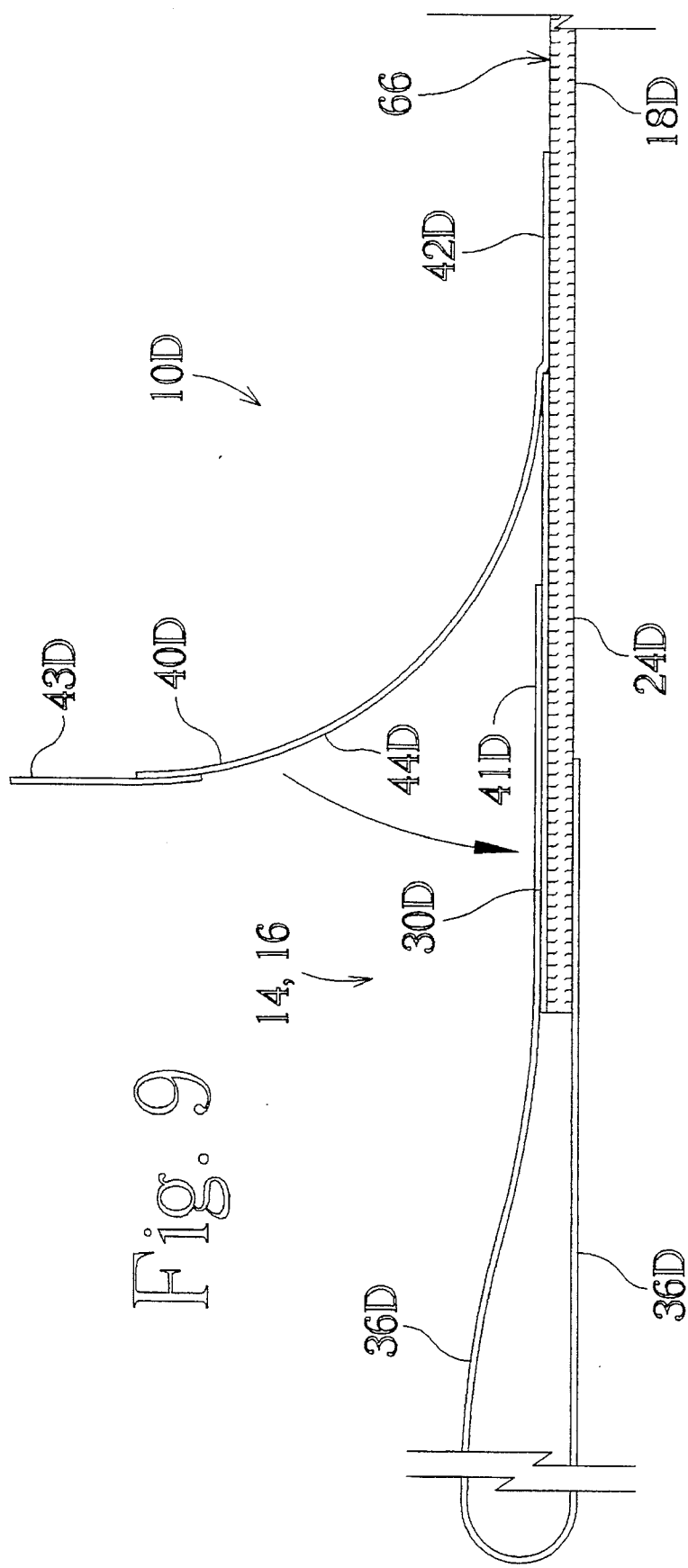

TRACHEOSTOMY TUBE HOLDER AND ASSOCIATED TUBE HOLDING METHOD

This application in part discloses and claims subject matter disclosed in my earlier filed patent application Ser. No. 08/344,147, filed on Nov. 23, 1994.

TECHNICAL FIELD

This invention relates a tracheostomy tube holder for maintaining the position of a tracheostomy tube as such tube is received in the trachea of a patient, and an associated tube holding method. In this particular invention the tracheostomy tube includes first and second tube engaging assemblies disposed at opposite ends of a securing strap which is received about the neck of a patient.

BACKGROUND ART

A tracheostomy is a fairly common surgical procedure for overcoming a tracheal obstruction. The procedure involves cutting into the trachea through the neck tissues to allow the insertion of a tracheostomy tube. Once the tracheostomy tube has been inserted it is important that the position of the tube be stabilize such that it is not inadvertently withdrawn from the trachea, and such that the tube is otherwise positioned to function properly. Further, movement of the tracheostomy tube can cause discomfort to the patient. Heretofore, twill tape, a thin cotton shoe string-type material, has been used to secure the position of tracheostomy tubes. In this regard, a length of twill tape is received about the patients neck and tied at its opposite ends to a plate or flange provided on the tracheostomy tube. However, the thin twill tape, particularly when tied tight enough to securely hold the tube, can cause discomfort to the patient. Further, it is important in dealing with fresh tracheostomy tubes that the tube not be manipulated or moved more than necessary such that the stoma is given an opportunity to heal over. Because the ends of the twill tape are tied to the tracheostomy tube, it can be difficult to disengage the twill tape from the tube when the tape is being replaced without manipulating or moving the tube. Accordingly, tube holders have been designed in an effort to more effectively stabilize tracheostomy tubes. An example of such a device is disclosed in U.S. Pat. No. 4,331,144, a commercial embodiment of which is produced by Dale Medical Products, Inc., of Plainville, Mass. However, the device of this patent utilizes hook and loop-type fasteners to engage the tracheostomy tube, and these fasteners tend to disengage when pressure is exerted on them resulting in inadvertent failure of the device. At the same time, such hook and loop fasteners can be difficult to disengage without manipulation and movement of the tracheostomy tube. Further, the hook and loop-type fasteners are expensive and tend to collect dirt and contaminants so as to make the device difficult to clean or otherwise maintain in a sanitary condition. Other holding devices are disclosed in U.S. Pat. Nos. 5,009,227; 4,774,944; 4,744,358; 4,489,723; 4,351,311; 4,249,529; 3,927,676; 4,932,9434; 836,200; 5,037,397; 4,823,789; 3,046,989; U.S. Des. Pat. No. 310,721; 5,215,532; 4,690,675; 4,583,976; 4,333,468; 4,142,527; 4,120,304; 3,977,407; and 3,826,254.

Therefore, it is an object of the present invention to provide a tracheostomy tube holder for being received about a patient to maintain the position of a tracheostomy tube.

It is another object of the present invention to provide tracheostomy tube holder which is quickly and easily secured to, or released from, the tracheostomy tube, yet holds the tracheostomy tube firmly in position.

A further object of the present invention is to provide a tracheostomy tube holder which can be disengaged from the tracheostomy tube for cleaning or replacement, and re-secured to the tracheostomy tube, without undue manipulation or movement of the tracheostomy tube.

It is another object of the present invention to provide a tracheostomy tube holder which is adjustable from both ends and has tube engaging straps which stay secured to the tracheostomy tube holder while the remainder of the holder is being cleaned or replaced.

Yet another object of the present invention is to provide a tracheostomy tube holder which is easily adjustable to accommodate patients of different size.

Still another object of the present invention is to provide tracheostomy tube holder which is inexpensive to manufacture, increases patient comfort, and which can be easily cleaned.

SUMMARY OF THE INVENTION

Other objects and advantages will be accomplished by the present invention which provides a tracheostomy tube holder for being received about a patient for maintaining the position of a tracheostomy tube. The tube holder includes first and second tube engaging assemblies for engaging the tracheostomy tube. Each of the tube engaging assemblies has a first foundation strap defining an outer bonding surface proximate its distal end portion, and includes a tube engaging strap for engaging the tracheostomy tube, with the tube engaging strap having a distal end for being positioned on the first bonding surface. Each of the tube engaging assemblies further includes a locking strap having a proximal end secured to the foundation strap and defining an inner adhesive surface for releasably engaging both the distal end of the tube engaging strap and the outer bonding surface of the foundation strap. The tracheostomy tube holder also includes a securing strap having a first end portion secured to the proximal end portion of one foundation strap, and having a second end portion secured to the proximal end portion of the other foundation strap, whereby the tracheostomy holder is secured about the neck of the patient. Thus, in accordance with the method of the present invention the tube engaging straps of each tube engaging assembly are secured to the tracheostomy tube, and the distal end portions of the tube engaging straps are positioned on the operatively associated outer bonding surface provided on the foundation strap. The locking straps are then secured over the distal ends of the operatively associate engaging straps and outer bonding surfaces, thereby securing the tube engaging assemblies to the tracheostomy tube.

BRIEF DESCRIPTION OF THE DRAWINGS

The above mentioned features of the invention will be more clearly understood from the following detailed description of the invention read together with the drawings in which:

FIG. 1 illustrates a perspective view of a tracheostomy tube holder of the present invention.

FIG. 2A illustrates a partial front elevation view of a tracheostomy tube holder of the present invention.

FIG. 2B illustrates a partial front elevation view of a tracheostomy tube holder of the present invention.

FIG. 2C illustrates a partial front elevation view of a tracheostomy tube holder of the present invention.

FIG. 2D illustrates a partial front elevation view of a tracheostomy tube holder of the present invention.

FIG. 3 illustrates an exploded plan view of a tube engaging assembly of a tracheostomy tube holder of the present invention.

FIG. 7 illustrates a front elevation view of a further alternate embodiment of the tracheostomy tube holder of the present invention.

FIG. 8 illustrates a rear elevation view of a further alternate embodiment of the tracheostomy tube holder of the present invention.

FIG. 9 illustrates a partial plan view of a further alternate embodiment of the tracheostomy tube holder of the present invention.

BEST MODE FOR CARRYING OUT THE INVENTION

Figure 4:
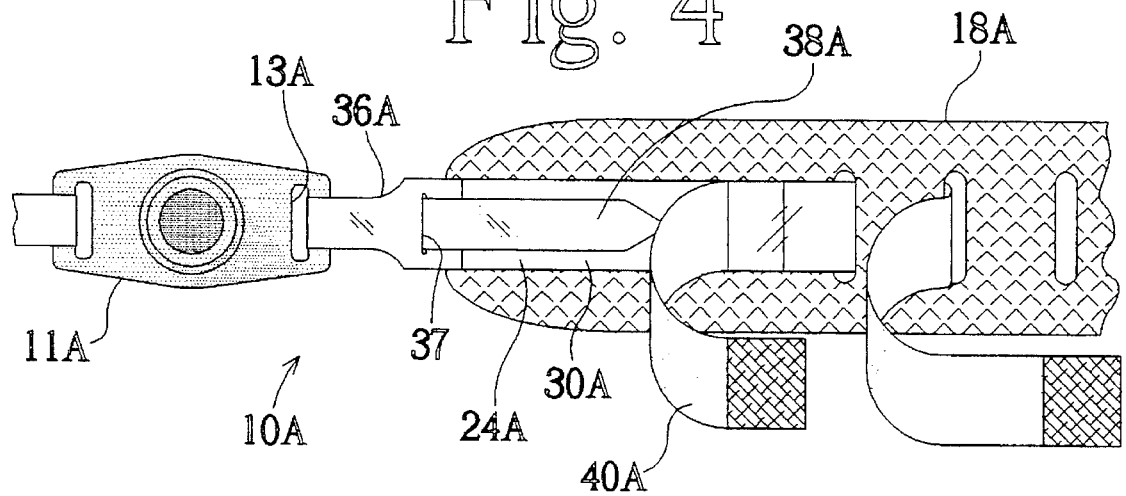
FIG. 4 illustrates a partial front elevation view of a tube engaging assembly of an alternate embodiment of the tracheostomy tube holder of the present invention.

A tracheostomy tube holder incorporating various features of the present invention is illustrated generally at 10 in the FIGS. The tube holder 10 is designed to releasably secure the position of a tracheostomy tube, such as the illustrated tube 1, as such tube is received through the skin and muscles of the neck and into the trachea of a patient. In this regard, conventional tracheostomy tubes 11 are provided with a flange or plate 12 which is provided with a pair of openings 13 to facilitate the attachment of holding devices. As will be discussed further below, the tube holder 10 releasably engages the plate 12 and, thereby, secures the position of the tracheostomy tube 11.

As illustrated in the Figures, the tube holder 10 includes first and second tube engaging assemblies 14 and 16, respectively, for releasably engaging the tracheostomy tube 11. The tube engaging assemblies 14 and 16 are secured to the first and second opposite end portions 20 and 22, respectively, of a securing strap 18, with the securing strap 18 being releasably received around the neck of the patient.

More specifically, each of the tube engaging assemblies 14 and 16 includes a flexible foundation strap 24 having a distal end portion 26 and a proximal end portion 28. In the preferred embodiment the foundation straps 24 are fabricated of a soft pliable material, such as a spun-bond polypropylene, having a surface 25 covered with a cellophane or plastic coating. As illustrated in FIG. 3, the surface 25 can be produced by bonding a piece of cellophane or plastic tape 27 to the foundation strap 24. It will be recognized that providing the cellophane or plastic coating prohibits the foundation straps 24 from absorbing bodily fluids or other contaminants and facilitates the cleaning of the foundation straps 24.

Each of the foundation straps 24 also defines a smooth, substantially non-porous outer bonding surface 30 proximate its distal end portion 26. As is best illustrated in FIG. 3, in the preferred embodiment a length of cellophane or plastic-backed adhesive tape 32 having an inner adhesive covered surface 34 (such as 3-M$^R$ 9921 bonding panel tape) is secured proximate the distal end portion 26 of the foundation strap 24 so as to provide the bonding surface 30.

A tube engaging strap 36 is secured to the distal end portion 26 of the foundation strap 24 which, and in accordance with the method of the present invention the tube engaging strap 36 is received through one of the openings 13 of the tube 11. After the tube engaging strap 36 is received through the opening 13, its distal end portion 38 is positioned on the bonding surface 30 of the foundation strap 24 as illustrated in FIG. 2B. In order to secure the distal end 38 of the tube engaging strap 36 to the foundation strap 24, a locking strap 40 is provided. The locking strap 40 has a proximal end 42 which is secured to the foundation strap 24 at a point displace from the distal end of the foundation strap 24, and defines a inner adhesive surface 44 for releasably bonding to the bonding surface 30, and to the tube engaging strap 36. In this regard, as the distal end portion 38 of the tube engaging strap 36 is positioned on the bonding surface 30, the locking strap 40 is brought into contact with both the bonding surface 30 adjacent the strap 36 and the strap 36 as illustrated in FIG. 2C, thereby locking the distal end portion 38 between the foundation strap 24 and the locking strap 40.

In order to facilitate the releasable engagement of the tube engaging strap 36 by the locking strap 40, the tube engaging strap 36 is preferably provided with a smooth, substantially non-porous outer bonding surface 46. As illustrated in FIG. 3, in the preferred embodiment the tube engaging strap 36 is fabricated of a synthetic woven fabric interposed between lengths of cellophane or plastic-backed adhesive tape 48 and 50 having an inner adhesive covered surfaces 52, such as 3-M$^R$ 9921 bonding panel tape. The tube engaging straps 36 can also be fabricated of a solid, non-porous plastic or vinyl. Accordingly, the tape 48 provides the bonding surface 46, and with both sides of the strap 36 provided with a smooth, substantially non-porous surface, the tube engaging strap 36 can be quickly and easily cleaned. It will also be noted that the tube engaging straps 36 are preferably narrower in width than the operatively associated bonding surfaces 30 and the locking straps 40. This construction insures that the tube engaging straps 36 are firmly secured between the bonding surfaces 30 and the locking straps 40.

Further, the distal ends 41 of the locking straps 40 can be provided with tab members 43 which define an area which is free of adhesive, and preferably of increased thickness, so as to facilitate the manipulation of the distal ends 41 and the releasable securing of the locking straps 40 to the bonding surfaces 30 and the tube engaging straps 36.

As noted above, the securing strap 18 serves to secure the holder 10 about the neck of the patient so as to maintain the position of the tube engaging assemblies 14 and 16, and, thus, the tube 11 engaged thereby. In this regard, in the preferred embodiment adjustable securing mechanisms are provided for securing the each of the tube engaging assemblies 14 and 16 to the opposite ends 20 and 22 of the securing strap 18 such that the length of the holder be is adjustable to accommodate different patients.

More specifically, in the preferred embodiment the securing strap 18 is provided with selectively spaced openings 54 for selectively receiving therethrough the proximal end portions 28 of the foundation straps 24. As illustrated in FIGS. 2A–D, the proximal end portions 28 are received inwardly through one opening 54 and outwardly through an adjacent opening 54. Each of the proximal end portions 28 has an adhesive surface 56, which in the preferred embodiment is defined by a length of double sided adhesive tape 58, such as, for example, Flexcon H-566, 3 mil tape. Further, the foundation straps 24 and the outer surface of the locking straps 40 are provided with a smooth, substantially non-porous, outer bonding surface 60 to which the adhesive surface 56 can be releasably secured after the proximal end portion 28 has been received through the openings 54. (See FIG. 2D). In the preferred embodiment the bonding surfaces 60 are defined by lengths of plastic or cellophane tape 62, such as, for example, 3-M$^R$ 9921 bonding panel tape, which are secured to the foundation straps 24 and locking straps 40, as illustrated in FIG. 3.

Thus, it will be recognized that by selecting the openings 54 to be used, and by selecting the position along the bonding surfaces 60 at which the adhesive surfaces 56 are secured, the effective length of the holder 10 can be changed to accommodate different patients and to effect a tightening or loosening of the holder 10 as it is positioned about a patient's neck. It will be noted that the proximal end portions 28 of the foundation straps 24 can be provided with tab members 64 which define an area which is free of adhesive, and preferably of increased thickness, so as to facilitate the manipulation of the proximal end portions 28 and the adjustable securing of the tube engaging assemblies 14 and 16 to the securing strap 18.

In the preferred embodiment the securing strap 18 is fabricated of a spun-bond polypropylene material which is soft, breathable, inexpensive, and comfortable to the patient. However, other suitable materials can be used if desired.

In FIG. 4 an alternated embodiment of the tube engaging strap of the present invention is illustrated at 36A. In this alternate embodiment the strap 36A is provided with a slot 37 for receiving therethrough the distal end 38A of the strap 36A. Accordingly, the engaging strap 36A is secured to the tracheostomy tube 11A by passing the distal end 38A through an opening 13A and back through the slot 37, whereupon the distal end 38A is secured between the operatively associated bonding surface 30A and locking strap 40A. By providing the slot 37, and directing the distal end 38A of the strap 36A upwardly through the slot 37 before it is received between the bonding surface 30A and locking strap 40A, inadvertent outward movement of the tube engaging strap 36A which would disengage the locking strap 40A from the bonding surface 30A is prohibited.

Figure 5:
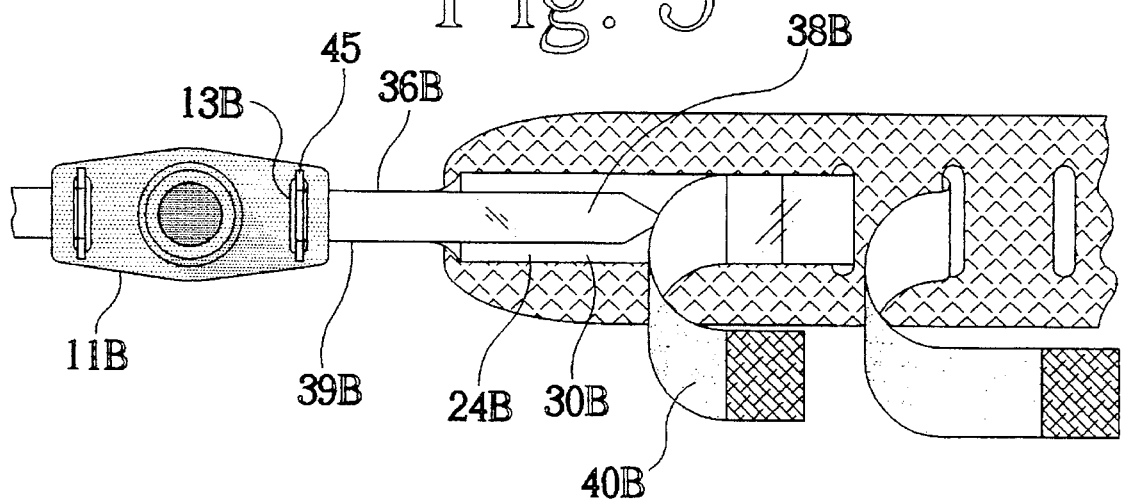
FIG. 5 illustrates a partial front elevation view of a tube engaging assembly of an alternate embodiment of the tracheostomy tube holder of the present invention.
Figure 6:
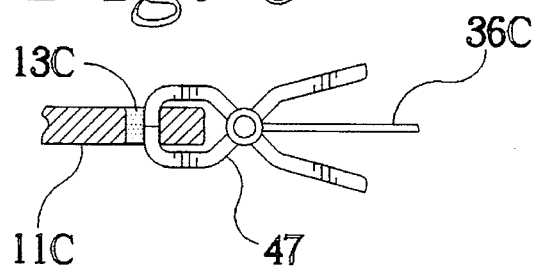
FIG. 6 illustrates a partial side elevation view of a tube engaging assembly of an alternate embodiment of the tracheostomy tube holder of the present invention.

Yet another alternated embodiment of a tube engaging strap of the present invention is illustrated at 36B in FIG. 5. In this alternate embodiment the end portion 39B is not secured to the foundation strap 24B, but instead is provided with a stop member 45 which is configured such that it will not pass through an opening 13B of the tracheostomy tube 11B. Accordingly, the tube engaging strap 36B is secured to the tube 11B by inserting the distal end 38B through the opening 13B and securing the distal end 38B between the bonding surface 30B and the locking strap 40B. Further, as illustrated in FIG. 6, a clamp member, such as the illustrated spring biased clamp 47, can be used instead of the stop member 45 to engage the tube 11C if desired. The construction of the engaging straps 36B and 36C can be particularly advantageous since it allows the engaging straps 36B to remain secured to the tube 11 while the remaining components of the tube holder are removed for cleaning or replaced. Thus, minimal manipulation or movement of the tube 11 is necessary.

In FIGS. 7–9 a further alternate embodiment of the tube holder of the present invention is referenced generally at 10D. For convenience, features and components of the holder 10D which are common to the holder 10 discussed above are referenced with common numerals followed by the alphabetic character "D".

Whereas in the preferred illustrated embodiment of the holder 10 the foundation straps 24 and the securing strap 18 define separate components, in the alternate embodiment of FIGS. 7–9 the holder 10D is provided with a foundation body 66 which integrally defines a securing strap portion 18D and oppositely disposed foundation strap portions 24D. In this regard, the proximal ends 42D of the locking straps 40D are secured to the foundation body 66 proximate the foundation strap portions 24D and serve to engage the tube engaging straps 36D and the bonding surface 30D as described above with respect to the holder 10. However, in this embodiment the relative positions of the securing strap portion 18D and foundations strap portions 24D are fixed, and the overall length of the holder 10D is adjusted by altering the length of, or the secured position of, the tube engaging straps 36D. For example, upon manufacture the holder 10D can be provided the largest of patients, and the straps 36D can be shortened, as by cutting, to accommodate the particular patient when the holder 10D is used.

It will be recognized by those skilled in the art that the holder 10D can incorporate the alternative tube engaging straps disclosed in FIGS. 4–6 if desired, and the tube engaging straps 36D are illustrative of only one preferred tube engaging strap which can be used.

In light of the above it will be recognized that the present invention provides a tracheostomy tube holder having great advantages over the prior art. However, while a preferred embodiment has been shown and described, it will be understood that there is no intent to limit the invention to such disclosure, but rather it is intended to cover all modifications and alternate constructions falling within the spirit and scope of the invention as defined in the appended claims.

I claim:

1. A tracheostomy tube holder for maintaining the position of a tracheostomy tube having a flange with first and second openings, said tube holder comprising:

a foundation body for being received about the neck of a patient, said foundation body defining a securing strap portion and oppositely disposed first and second foundation strap portions, each said first and second foundation strap portion defining a distal end portion and a bonding surface;

a first tube engaging assembly for engaging the tracheostomy tube, said first tube engaging assembly including a first tube engaging strap for being received through said first opening in the tracheostomy tube flange and having a distal end portion for being positioned on said bonding surface of said first foundation strap portion, said first tube engaging assembly further including a first locking strap defining an inner adhesive surface for releasably engaging said distal end portion of said first tube engaging strap and said bonding surface of said first foundation strap portion, whereby said distal end portion of said first tube engaging strap is releasably secured between said first foundation strap portion and said first locking strap, thereby securing said first tube engaging assembly to said tracheostomy tube; and a second tube engaging assembly for engaging the tracheostomy tube, said second tube engaging assembly including a second tube engaging strap for being received through said second opening in the tracheostomy tube flange and having a distal end portion for being positioned on said bonding surface of said second foundation strap portion, said second tube engaging assembly further including a second locking strap defining an inner adhesive surface for releasably engaging said distal end portion of said second tube engaging strap and said bonding surface of said second foundation strap portion, whereby said distal end portion of said second tube engaging strap is releasably secured between said second foundation strap portion and said second locking strap, thereby securing said second tube engaging assembly to said tracheostomy tube.

2. The tracheostomy tube holder of claim 1 wherein said bonding surfaces of said first and second foundation strap portions define smooth, substantially non-porous surfaces.

3. The tracheostomy tube holder of claim 1 wherein said first tube engaging strap is provided with a smooth, substantially non-porous bonding surface for engaging said inner adhesive surface of said first locking strap, and wherein said second tube engaging strap is provided with a smooth, substantially non-porous bonding surface for engaging said inner adhesive surface of said second locking strap, whereby the releasable engagement of said first and second locking straps with said distal end portions of said first and second tube engaging straps, respectively, is facilitated.

4. The tracheostomy tube holder of claim 1 wherein said first tube engaging strap defines a slot for receiving therethrough the distal end portion of said first tube engaging strap after said distal end portion of said first tube engaging strap has been received through said first opening in the tracheostomy tube flange, and wherein said second tube engaging strap defines a further slot for receiving therethrough said distal end portion of said second tube engaging strap after said distal end portion of said second tube engaging strap has been received through said second opening in the tracheostomy tube flange.

5. The tracheostomy tube holder of claim 1 wherein each said first and second tube engaging strap defines a proximal end portion and said proximal end portion of said first tube engaging strap carries a stop member whereby said distal end portion of said first tube engaging strap is received through said first opening in the tracheostomy tube flange and said stop member engages the tracheostomy tube flange and prohibits said proximal end portion from being received through the first opening, and wherein said proximal end portion of said second tube engaging strap carries a further stop member whereby said distal end portion of said second tube engaging strap is received through said second opening in the tracheostomy tube flange and said stop member engages the tracheostomy tube flange and prohibits said proximal end portion of said second tube engaging strap from being received through the second opening.

6. A method for securing the position of a tracheostomy tube having a flange with first and second openings as the tracheostomy tube is received in the trachea of a patient, said method utilizing a tracheostomy tube holder having a foundation body for being received about the neck of a patient, the foundation body defining first and second oppositely disposed foundation strap portions, the tube holder further including first and second tube engaging straps and first and second locking straps, said method comprising the steps of:

inserting the first tube engaging strap through said first opening in the tracheostomy tube flange;

positioning a distal end portion of the first tube engaging strap on a first bonding surface provided on the first foundation strap portion;

securing an inner adhesive surface of the first locking strap to the first bonding surface whereby the distal end portion of the first tube engaging strap is releasably secured between the first foundation strap portion and the first locking strap;

inserting the second tube engaging strap through said second opening in the tracheostomy tube flange;

positioning a distal end portion of the second tube engaging strap on a second bonding surface provided on the second foundation strap portion; and securing an inner adhesive surface of the second locking strap to the distal end portion of the second tube engaging strap and to the second bonding surface whereby the distal end portion of the second tube engaging strap is releasably secured between the second foundation strap and the second locking strap.

7. A tracheostomy tube holder for maintaining the position of a tracheostomy tube having a flange with first and second openings, said tube holder comprising:

a foundation body for being received about the neck of a patient, said foundation body defining a securing strap portion and oppositely disposed first and second foundation strap portions, each said first and second foundation strap portion defining a distal end portion;

a first tube engaging assembly for engaging the tracheostomy tube, said first tube engaging assembly including a first tube engaging strap for being received through the first opening in the tracheostomy tube flange and having a distal end portion for being positioned on said distal end portion of said first foundation strap portion, said first tube engaging assembly further including a first locking strap for releasably engaging said distal end portion of said first tube engaging strap and said distal end portion of said first foundation strap portion and including a first adhesive means for adhesively bonding said distal end portion of said first tube engaging strap between said first foundation strap portion and said first locking strap, thereby securing said first tube engaging assembly to said tracheostomy tube; and a second tube engaging assembly for engaging the tracheostomy tube, said second tube engaging assembly including a second tube engaging strap for being received through the second opening in the tracheostomy tube flange and having a distal end portion for being positioned on said distal end portion of said second foundation strap portion, said second tube engaging assembly further including a second locking strap for releasably engaging said distal end portion of said second tube engaging strap and said distal end portion of said second foundation strap portion and including a second adhesive means for adhesively bonding said distal end portion of said second tube engaging strap between said second foundation strap portion and said second locking strap, thereby securing said second tube engaging assembly to said tracheostomy tube.

8. The tracheostomy tube holder of claim 7 wherein said first adhesive means includes an adhesive surface portion provide on an inner surface of said first locking strap, and wherein said second adhesive means includes an adhesive surface portion provide on an inner surface of said second locking strap.

9. A method for securing the position of a tracheostomy tube having a flange with first and second openings as the tracheostomy tube is received in the trachea of a patient, said method utilizing a tracheostomy tube holder having a foundation body for being received about the neck of a patient, the foundation body defining first and second oppositely disposed foundation strap portions, the tube holder further including first and second tube engaging straps and first and second locking straps, said method comprising the steps of:

inserting the first tube engaging strap through the first opening in the tracheostomy tube flange;

positioning a distal end portion of the first tube engaging strap on the first foundation strap portion;

adhesively securing an inner surface of the first locking strap to the first foundation strap portion with the first tube engaging strap positioned therebetween, whereby the distal end portion of the first tube engaging strap is releasably secured between the first foundation strap portion and the first locking strap;

inserting the second tube engaging strap through the second opening in the tracheostomy tube flange;

positioning a distal end portion of the second tube engaging strap on the second foundation strap portion; and adhesively securing an inner surface of the second locking strap to the second foundation strap portion with the distal end portion of the second tube engaging strap positioned therebetween, whereby the distal end portion of the second tube engaging strap is releasably secured between the second foundation strap and the second locking strap.

* * * * *